United States Patent [19]

Yeh et al.

[11] 4,016,213
[45] Apr. 5, 1977

[54] RECOVERY OF PHENOL, ACETONE AND DIMETHYL PHENYL CARBINOL FROM CUMENE OXIDATION PRODUCT

[75] Inventors: Chuen Y. Yeh, Morristown; Francis L. Bohn, Morris Township, Morris County, both of N.J.

[73] Assignee: Allied Chemical Corporation, Morris Township, N.J.

[22] Filed: May 3, 1971

[21] Appl. No.: 139,875

[52] U.S. Cl. .......................................... 260/621 C
[51] Int. Cl.$^2$ ...................................... C07C 37/08
[58] Field of Search ........................... 260/621 C

[56] References Cited
UNITED STATES PATENTS

| | | | |
|---|---|---|---|
| 2,626,281 | 1/1953 | Joris | 260/621 C X |
| 2,663,735 | 12/1953 | Filar et al. | 260/621 C X |
| 2,683,751 | 7/1954 | Filar | 260/621 C |
| 2,993,074 | 7/1961 | Shepard | 260/621 C X |

Primary Examiner—Norman Morgenstern
Attorney, Agent, or Firm—Gerhard H. Fuchs; Michael S. Jarosz

[57] ABSTRACT

In the process for obtaining phenol and acetone from cumene hydroperoxide which has been obtained by liquid-phase oxidation of cumene with molecular oxygen, dehydration of by-product dimethyl phenyl carbinol to form alpha-methylstyrene and formation of higher boiling by-products, such as alpha-methylstyrene dimers and cumyl phenol, are substantially reduced by an improvement which comprises, in combination: decomposing the cumene hydroperoxide at temperatures in the range of from 65° to 105° C. using as decomposition catalyst sulfur dioxide or sulfuric acid in amount of between 0.002 and 0.02 percent by weight of the cumene hydroperoxide feed, conducting the decomposition in the absence of added water in a decomposition mixture containing not more than about 0.5 percent by weight of water, and withdrawing decomposition product at cumene hydroperoxide concentrations not exceeding about 0.5 percent by weight to obtain a decomposition product containing principally phenol and acetone, then adding a base to the decomposition product in excess of amount required to neutralize the decomposition catalyst and sufficient to adjust the pH of the product to from about 5 to about 9, followed by fractional distillation to separate the decomposition product into an acetone fraction, a phenol fraction and one or more by-product fractions, so that dehydration of dimethyl phenyl carbinol and formation of higher boiling reaction products of alpha-methylstyrene are substantially avoided during the decomposition and fractional distillation steps.

1 Claim, No Drawings

RECOVERY OF PHENOL, ACETONE AND DIMETHYL PHENYL CARBINOL FROM CUMENE OXIDATION PRODUCT

BACKGROUND OF THE INVENTION

This invention relates to an improvement in the treatment of cumene oxidation reaction mixture to raise the yields of phenol recoverable therefrom. More particularly, it relates to a process of decomposing cumene hydroperoxide and separating the decomposition product into its components comprising acetone, phenol and one or more by-products by fractional distillation wherein decomposition and fractional distillation are carried out under conditions such that dehydration of by-product dimethyl phenyl carbinol formed in the cumene oxidation step is substantially avoided with consequent reduction in formation of higher boiling by-products, such as alpha-methylstyrene dimers and cumyl phenol.

The production of phenol by oxidizing cumene with molecular oxygen in liquid phase in the presence or absence of added catalyst to obtain a solution of cumene hydroperoxide in cumene, followed by decomposition of the cumene hydroperoxide in the presence of catalysts, such as inorganic acids or $SO_2$ to obtain decomposition product containing phenol and acetone, and subsequent fractional distillation to separate the decomposition product into its components comprising acetone and phenol products, has been described. Cumene oxidation with elemental oxygen, e.g. oxygen of air, yields as the principal oxidation products cumene hydroperoxide together with lesser amounts of dimethyl phenyl carbinol and acetophenone in varying proportions. Under acidic conditions in the subsequent decomposition reaction, substantial portions of the dimethyl phenyl carbinol are dehydrated to form alpha-methylstyrene, which, in the subsequent distillation step, can be recovered as a separate product. However, dimethyl phenyl carbinol which has not been dehydrated in the decomposition step will gradually dehydrate throughout the subsequent distillation procedure as a result of which recovery of pure phenol is complicated. Further, alpha-methylstyrene formed under such conditions tends to react with phenol to form cumyl phenol, thereby reducing the yield of phenol product. Since boiling point of dimethyl phenyl carbinol (202° C.) is higher than that of phenol (boiling point 182° C.), it remains with the phenol fraction even after removal of the alpha-methylstyrene fraction (boiling point 161° C.) and continues to form alpha-methylstyrene within the phenol fraction after removal of the alpha-methylstyrene fraction. Since the alpha-methylstyrene so formed will remain with the phenol fraction, the purity of the phenol product is reduced. Further, under conventional conditions employed in fractionation of the cumene hydroperoxide decomposition product, alpha-methylstyrene tends to dimerize, forming a by-product for which there is no use.

Undesirability of presence of dimethyl phenyl carbinol during the distillation procedure has long been recognized. To remove the dimethyl phenyl carbinol, it has been proposed to dehydrate it during or subsequent to the cumene hydroperoxide decomposition step, but prior to separation of the alpha-methylstyrene fraction, as, e.g., by heating the decomposition product to elevated temperatures, preferably in the presence of acid catalysts. Under these conditions, however, dimerization of alpha-methylstyrene by-product and reaction of alpha-methylstyrene with phenol to form cumyl phenol tend to be favored, so that this method generally involves loss of desirable alpha-methylstyrene and phenol products.

It is known to neutralize the acid decomposition catalyst prior to subjecting the decomposition product to fractional distillation by methods such as passing the decomposition product over ion exchange resins, washing the decomposition product with water or alkali metal carbonate solutions, or adding alkali metal hydroxide in amount sufficient to neutralize the acid catalyst. It is known that presence of acid catalyst in the distillation procedure tends to catalyze formation of high boilers such as alpha-methylstyrene dimers and cumyl phenol.

In short, the prior art has attempted to solve the problems caused by presence of dimethyl phenyl carbinol in the cumene oxidation product, e.g. contamination of phenol product with alpha-methylstyrene, loss of alpha-methylstyrene by-product due to dimerization and loss of phenol product due to reaction of alpha-methylstyrene with phenol to form cumyl phenol, by dehydrating the dimethyl phenyl carbinol, and by neutralizing the acid decomposition catalyst, both prior to product distillation procedure.

It is an object of the present invention to provide an improved method for making phenol and acetone from cumene by oxidizing cumene to form cumene hydroperoxide, decomposing the cumene hydroperoxide to form a product comprising phenol and acetone, followed by fractional distillation to separate it into its components, wherein contamination of product phenol with alpha-methylstyrene is reduced, formation of high boiling by-products, such as alpha-methylstyrene dimers and cumyl phenol, is reduced, and wherein yields of product phenol are improved.

SUMMARY OF THE INVENTION

In accordance with the present invention, in the process for making phenol and acetone from cumene, formation of high boiling by-products is reduced, phenol yield is increased, and product phenol purity is improved by carrying out cumene hydroperoxide decomposition an subsequent fractional distillation under conditions such that dehydration of by-product dimethyl phenyl carbinol to alpha-methylstyrene is substantially avoided, so that a major portion of the dimethyl phenyl carbinol is carried unchanged through the decomposition and fractional distillation steps and can be recovered as by-product from the bottoms of the column wherein phenol is obtained as overhead product.

In accordance with the present invention, this is accomplished by an improvement in the process for obtaining phenol from cumene hydroperoxide, which has been obtained by liquid-phase oxidation of cumene with molecular oxygen, which involves forming a reaction mixture by continuously feeding the cumene hydroperoxide into a decomposer wherein the incoming hydroperoxide is diluted by cumene hydroperoxide decomposition products previously formed therein, maintaining the reaction mixture at elevated temperature, feeding to the reaction mixture a decomposition catalyst selected from the group consisting of sulfur dioxide and sulfuric acid, withdrawing reaction mixture from the decomposer, removing the decomposition catalyst from the product withdrawn from the decomposer, and fractionally distilling the resulting organic products to separately recover an acetone fraction, a phenol fraction and one or more by-product fractions, which improvement comprises, in combination (a) maintaining the reaction mixture in the decomposer at a temperature in the range of from 65° to 105° C.; (b) feeding the decomposition catalyst to the reaction mixture in amount of from 0.002 to 0.02 percent by weight of the cumene hydroperoxide feed; (c) conducting the decomposition reaction in the absence of added water so that the reaction mixture does not contain more than about 0.5 percent by weight of water, based on the weight of the reaction mixture; (d) withdrawing reaction mixture from the decomposer at cumene hydroperoxide concentrations not exceeding about 0.5 percent by weight, based on the weight of the reaction mixture; and (e) adding a base to the product withdrawn from the decomposer in excess of amount required to neutralize the decomposition catalyst and sufficient to adjust the pH of the product to from 5 to 9; so that dehydration of dimethyl phenyl carbinol to form alpha-methylstyrene is substantially avoided during the decomposition and distillation steps.

The dimethyl phenyl carbinol can be recovered from the bottoms of that distillation column wherein the phenol is obtained as overhead product. The dimethyl phenyl carbinol so obtained can, if desired, be dehydrated by known procedures to obtain alpha-methylstyrene as valuable by-product. In the production of phenol in accordance with the improved method of the present invention, phenol product yields are improved by substantial avoidance of reaction of alpha-methylstyrene with phenol to form cumyl phenol, phenol product quality is improved by reduction of contamination with alpha-methylstyrene formed therein by continued dehydration of dimethyl phenyl carbinol during the distillation step, and alpha-methylstyrene by-product losses are reduced by reduction of formation of its dimers.

DETAILED DESCRIPTION OF THE INVENTION

In the course of our studies we have investigated the effects of temperature, acidity and water concentration in liquid/acetone systems on (a) decomposition of cumene hydroperoxide to form phenol and acetone; (b) dehydration of dimethyl phenyl carbinol to form alpha-methylstyrene, (c) reaction of alpha-methylstyrene with phenol to form cumyl phenol, (d) formation of alpha-methylstyrene dimers from alpha-methylstyrene, (e) formation of cumyl phenol directly from dimethyl phenyl carbinol, and (f) formation of alpha-methylstyrene dimers directly from dimethyl phenyl carbinol. Our studies have confirmed that (1) at given acidity and water concentration, an increase in temperature increases the reaction rate of all of the reactions (a) through (f), above - with respect to cumene hydroperoxide decomposition to form phenol and acetone the reaction rate increases approximately 3.4 fold with temperature increase of 10° C. within the temperature range of about 35°–100° C.; (2) at given temperature and water concentration the rate of all of the reactions (a) through (f), above, increases with increase in acidity, i.e. increase in sulfur dioxide or sulfuric acid concentration; and (3) at given temperature and acidity the rate of all of reactions (a) through (f), above, increases with decreasing water concentration. We have determined the rate constants for all of the above reactions under various conditions (i.e. water concentration in the range of 0 to 10 percent by weight, temperatures in the range of 35° to 95° C., and acidity in the range of 30 to 300 ppm. of sulfuric acid), and we have found that with respect to the effect of water concentration on the rate constants of reactions (a) through (f), above, within the range of about 0.5 to 10 percent of water, the relationship appears to be linear with respect to any of these reactions. However, we have made the unexpected discovery that, with respect to reaction (a) only, i.e. decomposition of cumene hydroperoxide to form acetone and phenol, that linearity does not hold true for water concentrations below about 0.5 percent by weight. Thus, while for reactions (b) through (f), above, a decrease in water concentration in the range below 0.5 percent by weight of water leads only to that increase in reaction rate while would be predicted from reaction rates determined within the range of 0.5 to 10 percent by weight of water, the decomposition of cumene hydroperoxide does not follow that scheme but rather at water concentrations lower than about 0.5 percent by weight the reaction rates of the cumene hydroperoxide decomposition to form phenol and acetone are much greater than would be expected from extrapolation of the linear rate constant-/water concentration relationship obtained in the range of 0.5 to 10 percent water concentration. We have further studied the combined effect of temperature, acidity and water concentration on the rates of reactions (a) through (f), above, and, as the result of these detailed studies, in view of the unexpected effect of changes in water concentration on cumene hydroperoxide decomposition at low levels of water concentration below about 0.5 percent, we discussed conditions under which decomposition of cumene hydroperoxide to form phenol an acetone are favored, while at the same time dehydration of dimethyl phenyl carbinol to form alpha-methylstyrene dimers, and reaction of alpha-methylstyrene with phenol to form cumyl phenyl are substantially avoided. Thus, we found that by conducting the decomposition in media containing less than about 0.5 percent by water, by weight, preferably less than about 0.3 percent of water in combination with critical observation of decomposition temperatures in the range of from 65° to 105° C., preferably 75° to 95° C., and sulfuric acid or sulfur dioxide catalyst concentrations in amount of from 0.002 to 0.02 percent by weight of the cumene hydroperoxide feed, preferably of from 0.003 to 0.015 percent, it is possible to conduct decomposition of cumene hydroperoxide to form phenol and acetone so that dehydration of dimethyl phenyl carbinol to alpha-methylstyrene is substantially avoided, that is to say that less than the majority of the dimethyl phenyl carbinol contained in the cumene hydroperoxide mixture obtained from the oxidizer is dehydrated, while at the same time the rates of dimerization of alpha-methylstyrene and of reaction of alpha-methylstyrene with phenol to form cumyl phenol are decreased. At temperatures above about 105° C. dehydration of dimethyl phenyl carbinol proceeds rapidly under acidic conditions so that these temperatures must be avoided. At temperatures below about 65° C. decomposition of cumene hydroperoxide proceeds at commercially acceptable rates only at high levels of acidity which promote dehydration of dimethyl phenyl carbinol. For that reason we require that acid catalyst concentrations may not exceed 0.02 percent by weight, regardless of temperature, or else desired low levels of dimethyl phenyl carbinol dehydration cannot be maintained.

The terms "rate of reaction" and "rate constant", as used herein, are defined as set forth in K.J. Laidler, "Chemical Kinetics", McGraw-Hill Book Company, 2nd Ed. (1965) pp. 1-7.

The decomposition product obtained under the above-described conditions contains unchanged a major portion of the dimethyl phenyl carbinol formed in the oxidation step. This, at the current state of the art, would be considered highly undesirable. This is so because under conditions heretofore employed for separating the decomposition product into its components, which generally involves a first distillation step carried out under atmospheric pressure to separate the acetone, followed by one or more distillation steps to remove unoxidized cumene and alpha-methylstyrene, followed by a final distillation step to obtain the phenol as overhead product, wherein all distillation steps following separation of the acetone are generally conducted under reduced pressure at temperatures in the range of 130° to 165° C., most of the remaining dimethyl phenyl carbinol would be dehydrated to form alpha-methylstyrene. Since the rate of dehydration of dimethyl phenyl carbinol increases with increasing temperature, that rate would be highest in that column wherein phenol is obtained as the overhead product, i.e. at a point subsequent to separation of alpha-methylstyrene, so that the phenol product is contaminated with alpha-methylstyrene, and higher boiling reaction products of alpha-methylstyrene, i.e. its dimers and cumyl phenol are lost in the bottoms of the phenol product column. The art has taught that formation of higher boiling reaction products of alpha-methylstyrene, e.g. its dimers and cumyl phenol, can be substantially reduced by neutralizing the acid catalyst employed in the decomposition step prior to subjecting the decomposition mixture to fractional distillation. We now have found that by addition of a suitable base, preferably alkali metal hydroxide or phenate, in excess of amount required to completely neutralize the decomposition catalyst, and sufficient to adjust the pH of decomposition mixture to at least about 5 and preferably from about 6 to about 8, not only is dimerization of alpha-methylstyrene, and reaction of alpha-methylstyrene with phenol to form cumyl phenol substantially prevented, but, in addition thereto, dehydration of dimethyl phenyl carbinol to alpha-methylstyrene is reduced to insignificant level in the following fractional distillation where phenol product is recovered under reduced pressure. Therefore, prior to fractional distillation we add to the reaction mixture obtained by conducting decomposition of cumene hydroperoxide under the conditions of the present invention, above-described, a base, preferably alkali metal hydroxide or phenate, in amount sufficient to adjust its pH to at least about 5, so that dehydration of dimethyl phenyl carbinol will be reduced to insignificant level, and dimethyl phenyl carbinol will remain in, and can be recovered from, the still bottoms of the phenol product distillation column. If desired, additional base preferably alkali metal hydroxide or phenate, may be introduced into the phenol product distillation column.

The pH of the decomposition reaction mixture is determined in conventional manner at ambient temperature (25° C.) using pH Meter equipped with calomel/glass electrodes. Measurement is made directly in the decomposition reaction mixture.

Other than as expressly specified herein, the method of the present invention follows conventional procedures, and the apparatus employed is of conventional design. With respect to cumene hydroperoxide operation, desired hydroperoxide concentration in the range below about 0.5 percent by weight is maintained by feeding hydroperoxide into a decomposer in which the incoming hydroperoxide is diluted with cumene hydroperoxide decomposition products previously formed therein, and from which a reaction mixture of desired low hydroperoxide concentration is periodically or, preferably, continuously withdrawn. Sufficient agitation is employed in the decomposer to maintain a homogeneous reaction mixture therein, so that local build-up of hydroperoxide concentration is avoided. Hydroperoxide concentration within the decomposer can be controlled by varying temperature and/or catalyst concentration therein, or, preferably, by adjusting the flow of cumene hydroperoxide thereto. Cumene hydroperoxide concentration can be determined by conventional procedure, e.g. iodimetric titration or, preferably, by calorimetric determination as, for example, by continuously passing a small stream of decomposer contents through a calorimeter and introducing the entire catalyst stream to be added to the decomposer into the stream entering the calorimeter, so that, due to the high catalyst concentration, decomposition of the cumene hydroperoxide contained in that stream will be completed within the calorimeter, accompanied by corresponding evolution of heat. The temperature rise within the calorimeter is a quantitative measure of the hydroperoxide concentration. For example, at about 1 percent cumene hydroperoxide concentration in the decomposer an about 8° C. temperature rise will be observed in the calorimeter.

If desired, though it is necessary, the cumene hydroperoxide decomposition may be carried out in a series of two or more decomposers arranged in series wherein cumene hydroperoxide concentration is successively reduced in flow direction. For example, if two decomposers are employed, the cumene hydroperoxide concentration in the first decomposer may be maintained between about 3 and about 6 percent by weight. Reaction mixture withdrawn from that first decomposer is passed to a second decomposer wherein cumene hydroperoxide concentration is then reduced to the final desired concentration below about 0.5 percent, preferably between about 0 and about 0.3 percent by weight, based on the weight of the reaction mixture. In the event that more than one decomposer is employed, the decomposition catalyst may be fed to the first decomposer only, or it may be split between the first and successive decomposers. In the latter event, however, it is still necessary that the decomposition catalyst concentration within the first decomposer is at about 0.002 percent by weight. Second or successive decomposers need not be agitator-equipped. In a preferred embodiment employing two or more decomposers, most preferably two decomposers, all decomposers following the first agitated decomposer are of tubular design, that is to say comprise one or more tubes, provided with external heat exchange means, through which the decomposition mixture is passed.

The product withdrawn from the decomposer is immediately treated to neutralize the decomposition catalyst, followed by addition of base, preferably all alkali metal hydroxide or phenate, to adjust the pH thereof to at least about 5. Neutralization of decomposer catalyst is preferably accomplished by adding aqueous alkali metal hydroxide, i.e. a solution of about 5 to about 50 percent by weight of alkali metal hydroxide to the product under agitation, or by passing the decomposition mixture over an ion exchange resin, as is known to those skilled in the art. Following neutralization of decomposition catalyst, it is critically required that an excess of base, preferably alkali metal hydroxide or phenate be added, that is to say, more base than is required to completely neutralize the decomposition catalyst, and in amount sufficient to adjust the pH of the reaction mixture to at least about 5, so that dehydration of dimethyl phenyl carbinol during the following distillation steps may be avoided.

Following neutralization or removal of the decomposition catalyst, and addition of the required excess amount of base, the reaction mixture is subjected to fractional distillation in conventional manner to separate it into its components. In preferred operation, this involves first separating acetone by fractional distillation at about atmospheric pressure. After removal of the acetone, the reaction product is fractionally distilled in a series of columns operated under vacuum. Cumene is separated in a first column as overhead and the bottom product is fed to a second column wherein alpha-methylstyrene together with other hydrocarbons, e.g. remaining cumene, if any, is separated as overhead. The bottoms from the second column are fed to a third column wherein the phenol product is separated as overhead. As set forth above, additional base, preferably alkali metal hydroxide or phenate, may be added to the feed of the third column, i.e. the phenol column, in amount sufficient to increase the pH thereof to about 7. The bottom product of the phenol column, which contains the dimethyl phenyl carbinol, can be further separated into its components using known procedures.

The cumene hydroperoxide feed to the decomposer preferably contains at least about 70 percent by weight, more preferably yet about 80 percent by weight of cumene hydroperoxide. Since the product of oxidation of cumene with molecular oxygen generally contains only about 25 to 30 percent by weight of cumene hydroperoxide, it is preferably first, as is conventional, subjected to conditions effective to evaporate most of the unreacted cumene. As cumene hydroperoxide feed we prefer to employ a cumene hydroperoxide which has been obtained by oxidation of cumene in the absence of initiators, catalysts, additives or alkalizing agents. A method for oxidizing cumene to cumene hydroperoxide under such conditions is, for example, described in Argentinian Pat. No. 178,153. As described therein, cumene can be oxidized to cumene hydroperoxide in liquid phase using molecular oxygen-containing gas, such as air, in the absence of initiators, catalysts, additives or alkalizing agents by passing a molecular oxygen-containing gas stream through cumene having a purity of at least 99.8% in a single or multiple stage system which involves (a) continuously adding to a first reaction zone fresh cumene having a purity of at least 99.8%, (b) intimately contacting the cumene with oxygen by passing a continuous stream of oxygen-containing gas containing at least 8 mol percent of oxygen through each oxidizing zone at a rate such that the molar ratio of oxygen supplied to oxygen consumed exceeds 0.25 and the exit gases obtained from 3 to 10 percent by volume of oxygen, (c) maintaining the reaction temperature at about 80° to 120° C. and concentration of cumene hydroperoxide in the reaction mixture between about 8 to 40 percent by weight, (d) condensing the exit gases, separating the unoxidized cumene therefrom, treating the separated unoxidized cumene with an alkali metal hydroxide, and returning the cumene so treated for recycling.

DESCRIPTION OF THE PREFERRED EMBODIMENTS

The Examples described herein-below illustrate preferred procedure and set forth the best mode contemplated for carrying out the method of the present invention.

EXAMPLE I

Crude cumene hydroperoxide obtained by air oxidation of cumene followed by evaporation of most of the unreacted cumene containing about 80 percent by weight of cumene hydroperoxide, about 14 percent by weight of unreacted cumene, about 5 percent by weight of dimethyl phenyl carbinol, from about 0.08 to about 0.12 percent by weight of water, and about 1 percent by weight of acetophenone was subjected to decomposition by continuously running it into a stirred body of previously decomposed cumene hydroperoxide in a decomposer vessel at about 94° C. and with about 19 minutes hold-up time, together with about 30 parts by weight of concentrated sulfuric acid per million parts of crude cumene hydroperoxide introduced into the decomposer. The decomposition product mixture, continuously withdrawn from the bottom of the decomposer vessel, contained principally phenol and acetone together with 0.4 percent by weight of undecomposed cumene hydroperoxide, 2.38 percent by weight of alpha-methylstyrene, 2.69 percent by weight of dimethyl phenyl carbinol, 0.35 percent by weight of alpha-methylstyrene dimers and 0.39 percent by weight of cumyl phenol. It was calculated that 40 percent of the dimethyl phenyl carbinol fed to the decomposer had been dehydrated to alpha-methylstyrene.

To the decomposition product so obtained there is added a 50 percent aqueous solution of sodium hydroxide in amount sufficient to completely neutralize the sulfuric acid catalyst and to adjust the pH of the decomposition product to 7.0. The product is then fed to a first fractionating column operated at atmospheric pressure wherein acetone containing small amounts of water and organic impurities is driven off as overhead. The bottom product of the first fractionating column is fed to a second column operated at 170 mm. Hg. absolute pressure wherein unreacted cumene is separated as overhead product. The bottom product from the second fractionating column is fed to a third fractionating column operated at 190 mm. Hg. absolute pressure wherein alpha-methylstyrene is separated as overhead product. The bottom product of the third fractionating column contains substantially undehydrated all the dimethyl phenyl carbinol which had been fed to the first fractionating column. That bottom product is fed to a fourth fractionating column operated at 85 mm. Hg. absolute pressure, wherein phenol is obtained as overhead product. The phenol product contains less than 0.002 percent by weight of dimethyl phenyl carbinol, and less than 0.002 percent by weight of alpha-methylstyrene. Substantially all of the dimethyl phenyl carbinol fed to the first fractionating column is obtained in the bottoms product of the phenol product column.

COMPARATIVE TEST 1

The procedure of Example I was repeated using cumene hydroperoxide feed of identical composition to which there was added water in amount sufficient to adjust total water content to about 0.5 percent by weight employing decomposer temperature of 75° C., and using sulfuric acid catalyst in amount of 140 parts by weight per million parts of cumene hydroperoxide. The residence time in the decomposer vessel was 18 minutes. The decomposition product mixture, continuously withdrawn from the bottom of the vessel, contained principally phenol and acetone together with 0.1 percent by weight of undecomposed cumene hydroperoxide, 2.24 percent by weight of alpha-methylstyrene, 1.32 percent by weight of dimethyl phenyl carbinol, 0.73 percent by weight of dimethyl phenyl carbinol, 0.73 percent by weight of alpha-methylstyrene dimers and 0.70 percent by weight of cumyl phenol. It was calculated that of the total amount of dimethyl phenyl carbinol fed to the decomposer, 70 percent had been dehydrated to alpha-methylstyrene.

COMPARATIVE TEST 2

Comparative Test 1 was repeated using a decomposer temperature of 105° C., employing the sulfuric acid catalyst in amount of 60 parts per million parts of crude cumene hydroperoxide introduced in the decomposer, and adding water in amount sufficient to adjust total water content to about 0.7 percent by weight. The residence time within the decomposer was 20 minutes. The decomposition product mixture, continuously withdrawn from the bottom of the decomposer, contained principally phenol and acetone together with 0.1 percent by weight of undecomposed cumene hydroperoxide, 2.32 percent by weight of alpha-methylstyrene, 0.2 percent by weight of dimethyl phenyl carbinol, 1.69 percent by weight of alpha-methylstyrene dimers and 2.46 percent by weight of cumyl phenol. It was calculated that of the total amount of dimethyl phenyl carbinol fed to the decomposer, 97% had been dehydrated.

EXAMPLE II

Crude cumene hydroperoxide obtained by air oxidation of cumene followed by evaporation of most of the unreacted cumene containing about 80 percent by weight of cumene hydroperoxide, about 7 percent by weight of dimethyl phenyl carbinol, and about 0.1 percent by weight of water was subjected to decomposition by running it into an agitated decomposer vessel containing previously decomposed cumene hydroperoxide maintained at 85° C., and with about 15 minutes hold-up time, together with about 30 parts by weight of concentrated sulfuric acid per million parts of crude cumene hydroperoxide introduced into the decomposer vessel. The decomposition product mixture, continuously withdrawn from the agitated decomposer vessel, contained principally phenol and acetone, together with 3.65 percent by weight of undecomposed cumene hydroperoxide and 6.1 percent by weight of dimethyl phenyl carbinol. Of the total amount of dimethyl phenyl carbinol fed to the agitated decomposer vessel, 13 percent had been dehydrated to alpha-methylstyrene.

The composition product mixture withdrawn from the agitated decomposer vessel was passed continuously through a tube equipped with external means for heating and cooling ("plug flow decomposer") without external agitation at a temperature of 89° C., together with supplemental concentrated sulfuric acid catalyst in amount of about 60 parts by weight per million parts feed introduced into the plug flow decompower. Hold-up time within the plug flow decomposer was about 5 minutes. The decomposition product mixture continuously withdrawn from the plug flow decomposer contained principally phenol and acetone, together with 0.03 percent by weight of undecomposed cumene hydroperoxide, about 0.19 percent by weight of cumyl phenol, and about 5.8 percent by weight of dimethyl phenyl carbinol.

Of the total amount of dimethyl phenyl carbinol passed through the agitated decomposer vessel and subsequently through the plug flow decomposer, 17 percent had been dehydrated to alpha-methylstyrene.

EXAMPLE III

The procedure of Example II was repeated, but raising the temperature in the decomposition mixture in the plug flow decomposer to 95° C. The decomposition product continuously withdrawn from the plug flow decomposer contained principally phenol and acetone, together with 0.02 percent by weight of undecomposed cumene hydroperoxide, 0.23 percent by weight of cumyl phenol, and 5.0 percent by weight of dimethyl phenyl carbinol. Of the total amount of dimethyl phenyl carbinol passed through the agitated decomposer vessel and the plug flow decomposer, 29 percent had been dehydrated to alpha-methylstyrene.

COMPARATIVE TEST 3

Example II was repeated, except that the hold-up time in the agitated decomposer vessel was 17.5 minutes, and that the concentrated sulfuric acid fed to the agitated decomposer vessel amounted to 33 parts by weight per million parts of crude cumene hydroperoxide introduced into the decomposer vessel. The decomposition product mixture, continuously withdrawn from the agitated decomposer vessel to be fed into the plug flow decomposer, contained principally phenol and acetone, together with 1.53 percent by weight of undecomposed cumene hydroperoxide, 1.33 percent by weight of alpha-methylstyrene, 4.46 percent by weight of dimethyl phenyl carbinol, and 0.23 percent by weight of cumyl phenol. Of the total amount of dimethyl phenyl carbinol fed to the agitated decomposer vessel, 36 percent had been dehydrated.

As in Example II, the decomposition product withdrawn from the agitated decomposer vessel was continuously passed through the plug flow decomposer. Supplemental concentrated sulfuric acid catalyst added to the plug flow decompower feed mounted to 391 parts by weight per million parts of feed introduced into the decomposer. Temperature of the product continuously withdrawn from the plug flow decomposer was 98° C. That product contained principally phenol and acetone, together with undetectable amounts for undecomposed cumene hydroperoxide, 2.73 percent by weight of alpha-methylstyrene, 0.18 percent by weight of dimethyl phenyl carbinol, 1.21 percent by weight of alpha-methylstyrene dimers, and 1.51 percent by weight of cumyl phenol. Of the total amount of dimethyl phenyl carbinol passed through the agitated decomposer vessel and subsequently through the plug flow decomposer, more than 97 percent had been dehydrated.

Data relating to degree of dimethyl phenyl carbinol dehydration and formation of alpha-methylstyrene dimers and cumyl phenol by-products as obtained in Examples I through III and Comparative Tests 1 through 3, above, are summarized in Table I, below:

TABLE I

|  | Examples | | | Comparative Tests | | |
|---|---|---|---|---|---|---|
|  | I | II | III | 1 | 2 | 3 |
| %[1] DMPC[2] in feed | 5 | 7 | 7 | 5 | 7 | 7 |
| % DMPC in Decomposition Product | 2.7 | 5.8 | 5.0 | 1.3 | 0.2 | 0.2 |
| % DMPC Dehydrated | 40 | 17 | 29 | 70 | 97 | 97 |
| % AMS[3] Dimers in Decomposition Product | 0.4 | — | — | 0.7 | 1.7 | 1.2 |
| % CP[4] in Decomposition Product | 0.4 | 0.2 | 0.2 | 0.7 | 2.5 | 1.5 |
| % AMS in Decomposition Product | 2.4 | — | — | 2.2 | 2.3 | 2.7 |

[1]all percentages by weight
[2]dimethyl phenyl carbinol
[3]alpha-methylstyrene
[4]cumyl phenol.

The data summarized in Table I show that when decomposition of cumene hydroperoxide obtained by air oxidation of cumene to form principally phenol and acetone is carried out under the specific conditions required by the method of the present invention so that dehydration of dimethyl phenyl carbinol is substantially avoided in the decomposition step, then formation of higher boiling alpha-methylstyrene dimers and cumyl phenol by-products is minimal. These data show further that when decompositions of the cumene hydroperoxide is carried out under conditions such that the dimethyl phenyl carbinol is substantially dehydrated, then substantial amounts of undesirable alpha-methylstyrene dimers and cumyl phenol by-products are formed.

EXAMPLE IV

To illustrate that dehydration of dimethyl phenyl carbinol and formation of alpha-methylstyrene dimers and cumyl phenol by-products are substantially prevented under temperature conditions prevailing in fractional distillation to recover phenol product from cumene hydroperoxide decomposition product containing substantial amounts of undehydrated dimethyl phenyl carbinol in presence of added base in excess of amount required to completely neutralize the decomposition catalyst, a synthetic mixture representing phenol product distillation column contents was adjusted to pH 9 by addition of 0.1 percent by weight of sodium hydroxide and was maintained at 130° C. under atmospheric pressure for a period of 10 hours. Its composition was determined on periodic basis.

Results are summarized in Table II below:

TABLE II

| Elapsed Time Hr. | AMS[1]b Wt.% | AP[2] Wt.% | DMPC[3] Wt.% | Phenol Wt.% | AMS Dimers Wt.% | CP[4] Wt.% |
|---|---|---|---|---|---|---|
| 0[a] | 0.021[b] | 17.28 | 24.92 | 57.78 | — | — |
| 1.0 | 0.038 | 17.20 | 24.91 | 57.86 | — | — |
| 2.0 | 0.053 | 17.22 | 25.08 | 57.64 | — | — |
| 3.0 | 0.078 | 17.26 | 24.86 | 57.81 | — | — |
| 4.0 | 0.096 | 17.24 | 24.83 | 57.84 | — | — |
| 5.0 | 0.110 | 17.22 | 24.82 | 57.78 | 0.043 | 0.018 |
| 6.0 | 0.126 | 17.26 | 24.80 | 57.74 | — | — |
| 7.0 | — | — | — | — | 0.052 | 0.024 |
| 10.0 | — | — | — | — | 0.077 | 0.035 |

[1]alpha-methylstyrene
[2]acetophenone
[3]dimethyl phenyl carbinol
[4]cumyl phenol
[a]Sample was taken after 50 minutes of slow heating to reach 130° C.
[b]There was 0.02% of AMS in the charge before any heating. AMS was an impurity in dimethyl phenyl carbinol used for charge.

The synthetic mixture was substantially richer in acetophenone and dimethyl phenyl carbinol than the feed to phenol product distillation column in order to approximate conditions existing near the bottom of a continuously operated phenol product distillation column.

The data in Table II show that no appreciable amount of dimethyl phenyl carbinol is dehydrated, and only insignificant amounts of alpha-methylstyrene dimers and cumyl phenol are formed on recovery of the phenol product under conditions of the present invention.

Since various changes and modifications may be made in the invention without it departing from the spirit and essential characteristics thereof, it is intended that all matter contained in the above description shall be interpreted as illustrative only, the invention being limited only by the scope of the appended claims.

We claim:
1. In the process for obtaining phenol from cumene hydroperoxide, which has been obtained by liquid-phase oxidation of cumene with molecular oxygen, which involves forming a reaction mixture by continuously feeding the cumene oxidation product containing at least about 80 percent by weight of cumene hydroperoxide into a decomposer wherein the incoming hydroperoxide is diluted by cumene hydroperoxide decomposition products previously formed therein, maintaining the reaction mixture at elevated temperature, feeding to the reaction mixture a decomposition catalyst selected from the group consisting of sulfur dioxide and sulfuric acid, withdrawing reaction mixture from the decomposer, removing the decomposition catalyst from the product withdrawn from the decomposer, and fractionally distilling the resulting organic products to separately recover an acetone fraction, a phenol fraction and one or more by-product fractions, the improvement which comprises, in combination:
   a. conducting the process in two decomposers through which the reaction mixture is passed serially, wherein the first decomposer is equipped with a agitator, and wherein the second decomposer is a tubular decomposer;
   b. maintaining the reaction mixture in the decomposers at a temperature in the range of from 75° to 95° C.;
   c. feeding the decomposition catalyst to the reaction mixture in the first decomposer in amount of from 0.002 to 0.02 percent by weight of the cumene hydroperoxide feed;
   d. conducting the decomposition reaction in the absence of added water so that the reaction mixture does not contain more than about 0.3 percent by weight of water, based on the weight of the reaction mixture;

e. withdrawing reaction mixture from the first decomposer at cumene hydroperoxide concentration of between about 3 and about 6 percent by weight, based on the weight of the reaction mixture, and withdrawing reaction mixture from the second decomposer at cumene hydroperoxide concentrations not exceeding about 0.3 percent by weight, based on the weight of the reaction mixture; and f. adding a base selected from the group consisting of alkali metal hydroxides and alkali metal phenates to the product withdrawn from the second decomposer in excess of amount required to neutralize the decomposition catalyst and sufficient to adjust the pH of the product to from 6 to 8; so that dehydration of dimethyl phenyl carbinol to form alpha-methylstyrene is substantially avoided during the decomposition and distillation steps.

* * * * *